United States Patent
Dadheech et al.

(10) Patent No.: US 10,195,602 B2
(45) Date of Patent: Feb. 5, 2019

(54) NUCLEATION LAYERS FOR ENHANCING PHOTOCATALYTIC ACTIVITY OF TITANIUM DIOXIDE ($TiO_2$) COATINGS

(71) Applicant: GM Global Technology Operations LLC, Detroit, MI (US)

(72) Inventors: Gayatri Vyas Dadheech, Bloomfield Hills, MI (US); Thomas A. Seder, Fraser, MI (US); James A. Carpenter, Rochester Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 0 days.

(21) Appl. No.: 15/366,991

(22) Filed: Dec. 1, 2016

(65) Prior Publication Data

US 2018/0154345 A1    Jun. 7, 2018

(51) Int. Cl.
| | |
|---|---|
| *B01J 21/04* | (2006.01) |
| *B01J 21/06* | (2006.01) |
| *B01J 35/00* | (2006.01) |
| *B01J 35/02* | (2006.01) |
| *B01J 37/00* | (2006.01) |
| *C07D 279/20* | (2006.01) |

(52) U.S. Cl.
CPC ............ *B01J 35/004* (2013.01); *B01J 21/04* (2013.01); *B01J 21/063* (2013.01); *B01J 35/023* (2013.01); *C07D 279/20* (2013.01)

(58) Field of Classification Search
CPC ........ B01J 21/04; B01J 21/063; B01J 35/004; B01J 35/023; B01J 37/00
See application file for complete search history.

(56) References Cited

U.S. PATENT DOCUMENTS

| | | | | |
|---|---|---|---|---|
| 6,037,289 A | * | 3/2000 | Chopin ................ | B82Y 30/00 |
| | | | | 106/287.16 |
| 6,362,121 B1 | * | 3/2002 | Chopin ................ | B82Y 30/00 |
| | | | | 106/287.16 |

(Continued)

OTHER PUBLICATIONS

Andrew Mills et al.; "Overview of the Current ISO tests for Photocatalytic Materials"; Journal of Photochemistry and Photobiology A: Chemistry; vol. 237, Jun. 1, 2012; 63 pages.

*Primary Examiner* — Cam N. Nguyen
(74) *Attorney, Agent, or Firm* — Harness, Dickey & Pierce, P.L.C.

(57) ABSTRACT

A photocatalytic system having enhanced photo efficiency/photonic efficacy is provided that includes a thin nucleation material coated on a substrate. The nucleation material enhances lattice matching for a subsequently deposited photocatalytic active material. Such a photocatalytic system may be used as a self-cleaning surface in an application where removal of fingerprints and other residue is desired. In certain aspects, the nucleation material comprises aluminum oxide ($Al_2O_3$) and the photocatalytic material comprises an anatase phase of titanium dioxide ($TiO_2$) deposited over the nucleation material. A photocatalytic activity of the system is ≥ about 50% above a comparative photocatalytic activity where the photocatalytic active material is disposed directly on the substrate. Methods of making such photocatalytic systems are also provided.

19 Claims, 3 Drawing Sheets

(56) References Cited

U.S. PATENT DOCUMENTS

| | | | | |
|---|---|---|---|---|
| 6,479,141 B1* | 11/2002 | Sanbayashi | ............ | B01J 35/002 106/436 |
| 6,592,842 B2* | 7/2003 | Elder | ................ | B01J 21/063 423/598 |
| 6,887,816 B2* | 5/2005 | Tanaka | ................ | B01J 21/063 428/220 |
| 7,414,009 B2* | 8/2008 | Tanaka | ................ | B01J 21/063 502/242 |
| 7,541,012 B2* | 6/2009 | Yeung | ................ | B01D 53/864 423/245.1 |
| 7,582,156 B2* | 9/2009 | Tanaka | ................ | B01J 21/063 106/286.4 |
| 7,691,781 B2* | 4/2010 | Inoue | ................ | B01J 21/063 423/610 |
| 8,501,132 B2* | 8/2013 | Fu | ................ | B82Y 30/00 423/239.1 |
| 2003/0235695 A1* | 12/2003 | Greenberg | ............ | C03C 17/245 428/432 |
| 2015/0162602 A1 | 6/2015 | Dadheech et al. | | |
| 2017/0056871 A1 | 3/2017 | Dadheech et al. | | |
| 2017/0232430 A1 | 8/2017 | Dadheech et al. | | |
| 2017/0327948 A1 | 11/2017 | Dadheech et al. | | |

* cited by examiner

NUCLEATION LAYERS FOR ENHANCING PHOTOCATALYTIC ACTIVITY OF TITANIUM DIOXIDE (TIO₂) COATINGS

INTRODUCTION

This section provides background information related to the present disclosure which is not necessarily prior art. The present disclosure relates to enhancing photocatalytic activity of titanium dioxide ($TiO_2$) by use of a nucleation layer that provides lattice matching to promote formation of desirable phases of $TiO_2$ having enhanced photocatalytic activity, such as anatase $TiO_2$. Methods of making $TiO_2$ having enhanced photocatalytic activity are also provided.

Various surfaces may come into contact with skin, such as touch screens, glasses, windows, camera lenses, appliances, mirrors, and the like. When such surfaces are touched by an animal, fingerprint oil and/or other organic residues can remain that are highly visible. Thus, it would be desirable to develop an active surface layer for such surfaces that serves to remove oil residue. $TiO_2$ may be used to catalyze a degradation reaction of oil or other organic residues on a surface by absorbing UV light and water from the atmosphere to release free radicals that react with and degrade the oil residues. It would be desirable to enhance the catalysis reaction to expedite degradation and removal of oil and organic residues from such a surface.

SUMMARY

This section provides a general summary of the disclosure, and is not a comprehensive disclosure of its full scope or all of its features.

In certain aspects, the present disclosure relates to a photocatalytic system that may include a nucleation material coated on a substrate. The nucleation material comprises a metal oxide compound, where the metal is selected from the group consisting of: aluminum, zirconium, niobium, cerium, vanadium, lanthanum, titanium, silicon, iron, cobalt, nickel, molybdenum, tungsten, and combinations thereof. A photocatalytic active material comprising an anatase phase of titanium dioxide ($TiO_2$) is deposited over the nucleation material. A photocatalytic activity of is greater than or equal to about 50% above a comparative photocatalytic activity where the photocatalytic active material is disposed directly on the substrate.

The photocatalytic system may further include the nucleation material having an average thickness of less than or equal to about 10 nm.

The photocatalytic system may further include the nucleation material being selected from the group consisting of: aluminum oxide ($Al_2O_3$), $SrTiO_3$ (STO), $LaAlO_3$ (LAO), Y stabilized $ZrO_2$ (YSZ), and combinations thereof.

The photocatalytic system may further include the nucleation material including aluminum oxide ($Al_2O_3$). In certain aspects, the aluminum oxide ($Al_2O_3$) comprises a $\theta$-$Al_2O_3$ phase having a monoclinic space group with lattice parameters of a=1.185 nm, b=0.295 nm and c=0.562 nm.

The photocatalytic system may further have a lattice mismatch of less than or equal to about 12% between the nucleation material and the photocatalytic active material.

The photocatalytic system may further include the active material having greater than or equal to about 50% by volume of anatase phase.

The photocatalytic system may further include the photocatalytic activity being greater than or equal to about 75% above the comparative photocatalytic activity where the active material is disposed directly on the substrate, In other aspects, the present disclosure provides a self-cleaning photocatalytic system including a substrate, a nucleation coating including aluminum oxide ($Al_2O_3$) disposed on the substrate having a thickness of less than or equal to about 10 nm, and an exposed surface comprising a photocatalytic active material that includes an anatase phase of titanium dioxide ($TiO_2$) deposited over the nucleation coating. The photocatalytic active material facilitates a decomposition reaction of any oil or organic residue on the exposed surface when in the presence of water and ultraviolet radiation.

The self-cleaning photocatalytic system may further include the self-cleaning photocatalytic system's photocatalytic activity being about 50% above a comparative photocatalytic activity where the photocatalytic active material is disposed directly on the substrate.

The self-cleaning photocatalytic system may further include the nucleation coating having an average thickness of greater than or equal to about 3 nm to less than or equal to about 5 nm.

The self-cleaning photocatalytic system may further include the photocatalytic active material including greater than or equal to about 50% by volume of the anatase phase of titanium dioxide ($TiO_2$).

The self-cleaning photocatalytic system may further include the substrate comprises glass or an anti-reflection coating.

The self-cleaning photocatalytic system may further include the exposed surface defining a plurality of islands of the photocatalytic active material distributed within a low surface energy polymeric material, where the nucleation coating is disposed beneath the photocatalytic active material, but is absent in the regions where the low surface energy polymeric material is present.

The self-cleaning photocatalytic system may further include a lattice mismatch is less than or equal to about 2% between the nucleation material and the photocatalytic active material.

The self-cleaning photocatalytic system may further include the aluminum oxide ($Al_2O_3$) including a $\theta$-$Al_2O_3$ phase having a crystal structure having a monoclinic space group with lattice parameters of a=1.185 nm, b=0.295 nm and c=0.562 nm that enhances lattice matching and formation of the anatase phase of titanium dioxide ($TiO_2$).

In yet other aspects, a method of enhancing photocatalytic activity in a photocatalytic system includes depositing a nucleation material coated on a substrate. The nucleation material includes a metal oxide compound. The metal is selected from the group consisting of: aluminum, zirconium, niobium, cerium, vanadium, lanthanum, titanium, silicon, iron, cobalt, nickel, molybdenum, tungsten, and combinations thereof. The method further includes depositing a photocatalytic active material including an anatase phase of titanium dioxide ($TiO_2$) over the nucleation material, wherein the nucleation material provides lattice matching to enhance formation of the anatase phase of titanium dioxide ($TiO_2$), so that a photocatalytic activity is greater than or equal to about 50% above a comparative photocatalytic activity where the photocatalytic active material is disposed directly on the substrate.

The method may further include the depositing of the nucleation material being a process selected from the group consisting of: atomic layer deposition (ALD), chemical vapor deposition (CVD), plasma enhanced chemical vapor deposition (CVD), physical vapor deposition (PVD), and combinations thereof.

The method may further include the depositing of the photocatalytic active material being a process selected from the group consisting of: atomic layer deposition (ALD), chemical vapor deposition (CVD), atmospheric pressure chemical vapor deposition (APCVD), low pressure chemical vapor deposition (LPCVD), plasma enhanced chemical vapor deposition (CVD), physical vapor deposition (PVD), magnetron sputtering, wet chemistry, sol-gel processes, and combinations thereof.

The method may further include depositing of the nucleation material is done by an atomic layer deposition process and the nucleation material has a thickness of less than or equal to about 10 nm.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
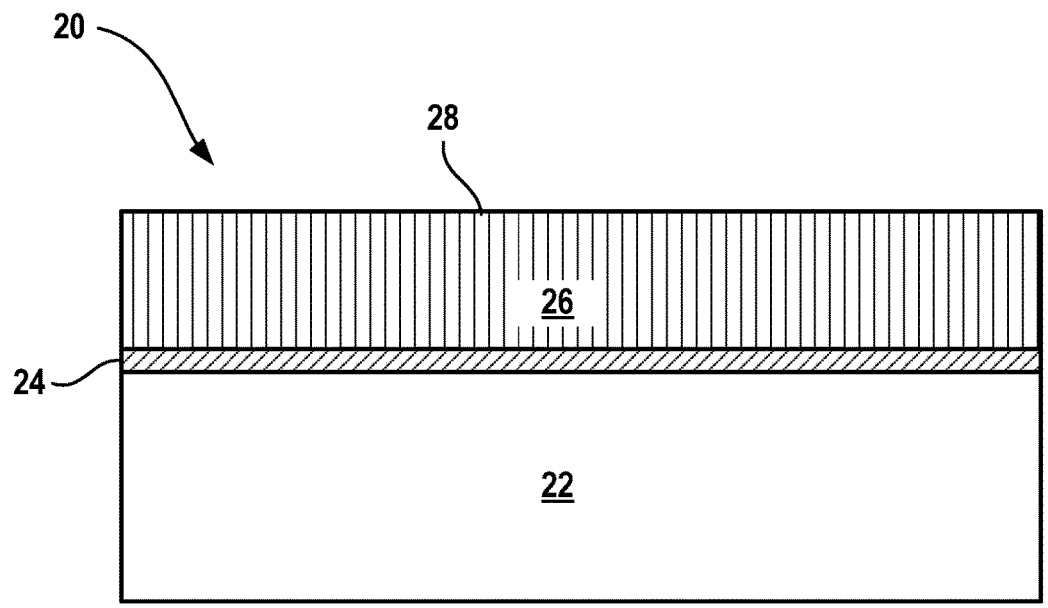
FIG. 1 shows a sectional side view of a photoactive system including a substrate, a nucleation layer, and a photoactive layer prepared in accordance with certain aspects of the present disclosure.

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

In various aspects, the present disclosure provides a photoactive system that may be a self-cleaning system 20. The self-cleaning system 20 includes a substrate 22 having a nucleation material coating 24 coated thereon as shown in FIG. 1. A photoactive layer 26 comprises a photocatalytic active material. The photocatalytic material 34 may provide an exposed surface 28 with self-cleaning capability. It should be noted that the nucleation material coating 24 and photoactive layer 26 may also form discrete regions on the exposed surface 28 rather than a continuous layer, as will be described further below. The photocatalytic active material in the photoactive layer 26 may oxidize and/or vaporize any organic material, e.g., squalene, present on the exposed surface 28, as set forth in more detail below. In particular, the photocatalytic active material may be a photocatalyst that is activated upon exposure to certain wavelengths of ultraviolet radiation, for example, visible light or ultraviolet light. Visible light has wavelengths ranging from about 390 to about 750 nm, while ultraviolet light has wavelengths from about 10 nm to about 390 nm.

For example, where the photoactive layer 26 of the self-cleaning system 20 is exposed to UV radiation, for example, having a wavelength below approximately 357 nm, in the presence of water (e.g., ambient humidity), the photocatalytic active material, e.g., $TiO_2$, is activated facilitating a photocatalytic reaction. A photocatalytic reaction may create an oxidation agent that breaks down the organic matter, e.g., squalene or other organic materials, to low chain hydrocarbons to carbon dioxide and water in the presence of the photocatalyst, electromagnetic radiation, e.g., ultraviolet light; and water, e.g., humidity from ambient conditions. As such, the photocatalytic active material accelerates a rate of the photocatalytic decomposition reaction.

By way of further detail, when electromagnetic radiation having a desired wavelength illuminates the photocatalytic active material in the photoactive layer 26, an electron from the valence band of the photocatalytic active material may promote to the conduction band of the photocatalytic active material, which in turn may create a hole in the valence band and an excess of negative charge or electron in the conduction band. The hole may promote oxidation and the electron may promote reduction. Generally, the hole may combine with water to produce a hydroxyl radical (.OH). The hole may also react directly with squalene or other organic material to increase an overall self-cleaning efficiency of the self-cleaning system 20. Similarly, oxygen in the ambient environment surrounding the photocatalytic active material may be reduced by the electron to form a superoxide ion (.$O_2^-$), which in turn may oxidize the organic material present on the exposed surface 28 of the self-cleaning system 20. In certain aspects, reaction byproducts may volatilize or otherwise be removed from the self-cleaning system 20.

In addition, the hole may become trapped before recombination with the electron. For such situations, the photocatalytic active material may be functionalized, for example by doping. The dopants may act as an electrocatalyst and may increase a transfer of electrons to oxygen molecules, which may in turn lower the occurrence of the recombination of electrons and holes.

Therefore, the self-cleaning system 20 may be characterized as self-cleaning so that the substrate 22 is protected from residue by removing, e.g., oxidizing and/or vaporizing the fingerprints, squalene, oils, and/or organic material deposited by touch of an operator. Consequently, the self-cleaning system 20 may enhance aesthetics, cleanliness, and readability of reflective or transparent surfaces for display systems, lenses, sensors, and the like.

In certain aspects, a source of electromagnetic radiation may be provided near the self-cleaning system 20 to direct light having a predetermined range of wavelengths at the photoactive layer 26 of the self-cleaning system 20. Alternatively or additionally, the self-cleaning system 20 may also be heated, for example by infrared radiation, to improve diffusion of the organic materials to facilitate reaction with photocatalytic active material in the photoactive layer 26.

Suitable photocatalytic active materials may include, but are not limited to, photo-oxidative semiconductors, semiconducting oxides, doped metal oxides, heterojunction materials, and combinations thereof. In one embodiment, the photocatalytic active material may be titanium dioxide ($TiO_2$) and may comprise an anatase phase, which may exhibit a comparatively higher photocatalytic activity than a rutile form of $TiO_2$. Tetragonal anatase $TiO_2$ has lattice parameters of c=0.951 nm and a=0.378 nm. As described below, where the photocatalytic active material comprises $TiO_2$, while the amount of anatase is desirably maximized, the $TiO_2$ may be may be present as a combination of the rutile form and the anatase form.

Further, the photocatalytic active material may be doped to form a functionalized photocatalytic material, for example, a functionalized titanium dioxide. By way of example, the functionalized photocatalytic active material may be doped with a metal such as, but not limited to, palladium, ruthenium, silver, chromium, cobalt, copper, vanadium, iron, silver, platinum, molybdenum, lanthanum, niobium, and combinations thereof. Alternatively, the functionalized photocatalytic material may be doped with a non-metal such as, but not limited to, nitrogen, sulfur, carbon, boron, potassium, iodine, fluorine, and combinations thereof.

In other non-limiting embodiments, the photocatalytic active material may include a semiconducting oxide such as, but not limited to, zinc oxide, bismuth, tin oxide, and combinations thereof. The semiconducting oxide may be selected to have a band gap separation suitable for a photocatalytic reaction, as set forth in more detail below.

The nucleation material coating 24 serves to enhance lattice matching of a subsequent active material layer comprising titanium dioxide ($TiO_2$) deposited thereon. More specifically, the nucleation material coating 24 promotes formation of desirable crystal structures with small lattice mismatch and phases of the photocatalytic active material subsequently deposited in the photoactive layer 26 over the nucleation material coating 24. In one variation, an anatase phase of the photocatalytic active material $TiO_2$ exhibits enhanced photocatalytic activity as compared to other phases of $TiO_2$, such as rutile or brookite phases. The lattice spacing presented by the nucleation layer 24 to the growing TiO2 film serves to promote anatase formation.

The nucleation layer 24 also substantially matches the surface energy of anatase $TiO_2$ for initiating the film growth at low temperatures below 400° C., optionally at greater than or equal to about 200° C. to less than or equal to about 350° C., and in certain aspects, optionally at 350° C.

In certain aspects, the photoactive layer 26 may comprise titanium dioxide, where greater than or equal to about 50% by volume of the titanium dioxide is present an anatase phase, optionally greater than or equal to about 60% by volume, optionally greater than or equal to about 70% by volume, optionally greater than or equal to about 80% by volume, optionally greater than or equal to about 90% by volume, and in certain variations, optionally greater than or equal to about 95% by volume of the titanium dioxide is present an anatase phase.

In certain variations, the photoactive layer 26 may have an average thickness of less than or equal to about 50 nm, optionally less than or equal to about 25 nm, optionally less than or equal to about 20 nm, optionally less than or equal to about 10 nm, optionally less than or equal to about 9 nm, optionally less than or equal to about 8 nm, optionally less than or equal to about 7 nm, optionally less than or equal to about 6 nm, and in certain variations, optionally less than or equal to about 5 nm. The photocatalytic activity of anatase $TiO_2$ increases with thickness nearly exponentially, saturating at about 5 nm, thus in certain variations, the average thickness may be about 5 nm to about 7 nm thick. It should be noted that the photoactive layer 26 is not limited to such dimensions and may indeed have a thickness above those listed above.

The nucleation material coating 24 may be thin, for example, having an average thickness of less than or equal to about 10 nm, optionally less than or equal to about 9 nm, optionally less than or equal to about 8 nm, optionally less than or equal to about 7 nm, optionally less than or equal to about 6 nm, and in certain variations, optionally less than or equal to about 5 nm. In certain aspects, the nucleation material coating 24 may have an average thickness of greater than or equal to about 3 nm to less than or equal to about 10 nm, optionally greater than or equal to about 3 nm to less than or equal to about 5 nm.

In certain aspects, the nucleation material coating 24 comprises a metal oxide compound having a crystal lattice structure with a lattice spacing that promotes growth of an anatase film during deposition. The lattice template of the nucleation material coating 24 is believed to promote formation and growth of the anatase $TiO_2$ phase at lower temperatures than are might otherwise be required. In certain aspects, the nucleation material coating 24 optimizes oriented nucleation growth required for the crystallinity and lattice matching with anatase $TiO_2$ while providing high adhesion and minimum stress. The metal oxide used as the nucleation material in the nucleation material coating 24 may comprise a metal selected from the group consisting of: aluminum, zirconium, niobium, cerium, vanadium, lanthanum, titanium, silicon, iron, cobalt, nickel, molybdenum, tungsten, and combinations thereof.

In certain variations, the nucleation material coating 24 comprises aluminum oxide or alumina ($Al_2O_3$) as the nucleation material. Where the nucleation material coating 24 comprises $Al_2O_3$ it may have a crystal lattice structure of a monoclinic space group with lattice parameters of a=1.185 nm, b=0.295 nm and c=0.562 nm. An advantageous nucleation material coating 24 comprises a high percentage of the $\theta$-$Al_2O_3$ phase. In certain aspects, the nucleation material provides lattice matching with the photocatalytic material deposited thereon. In certain aspects, such lattice matching can be understood to be a lattice mismatch between the nucleation material coating 24 and the photoactive layer 26 of less than or equal to about 15%, optionally less than or equal to about 12%, optionally less than or equal to about 10%, optionally less than or equal to about 8%, optionally less than or equal to about 5%, optionally less than or equal to about 4%, optionally less than or equal to about 3%, optionally less than or equal to about 2%, and in certain variations, optionally less than or equal to about 1%.

In other variations, epitaxial growth of anatase can also be promoted by $SrTiO_3$ (STO), $LaAlO_3$ (LAO), and Y stabilized $ZrO_2$ (YSZ) nucleation layers. STO has a cubic symmetry with a lattice parameter of a=0.39. Thus, STO has a similar lattice matching, with a mere mismatch of only 3.04% to the lattice of the growing anatase film. LAO is rhombohedral with lattice parameters of a=0.536 nm and c=1.311 nm. LAO presents a mismatch of only about 11.6% to the lattice of growing anatase film. YSZ is cubic with a lattice parameter of a=0.514 nm.

The nucleation material coating 24 may be deposited on the substrate 22 by atomic layer deposition (ALD), chemical vapor deposition (CVD), including atmospheric pressure chemical vapor deposition (APCVD), low pressure chemical vapor deposition (LPCVD), plasma enhanced chemical vapor deposition (CVD), physical vapor deposition (PVD), such as magnetron sputtering, wet chemistry, such as dip, spray or sol-gel processes, or other techniques known for depositing thin layers of metal oxides, such as $Al_2O_3$. In certain aspects, the metal oxide nucleation material coating 24 may be applied by an atomic layer deposition (ALD) process that can coat a substrate with a conformal layer that comprises the metal oxide layer, such as aluminum oxide ($Al_2O_3$). ALD is a self-limiting process for chemical deposition or growth of ultra-thin films on a substrate. The ALD chemical gas-phase thin film deposition method is advantageous mainly for the surface-controlled and self-saturating monolayer formation, which can create ultrathin conformal structures coating all surfaces of the substrate in a continuous film. ALD typically involves subjecting the target substrate to self-saturating surface reactions. For an aluminum oxide ($Al_2O_3$) coating, a precursor selected from the group consisting of: trimethyl aluminum (TMA (($CH_3)_3Al$)), triethyl aluminum (($C_2H_5)_3Al$), diethyl aluminum (($C_2H_5)_2AlCl$), tributyl aluminum (($C_4H_9)_3Al$), aluminum chloride ($AlCl_3$), aluminum ethoxide ($Al(OC_2H_5)_3$), aluminum isopropoxide ($Al(C_3H_7O)_3$), aluminum fluoride ($AlF_3$), aluminum nitride (($AlN$), where the precursor is TMA and ammonia), and the like. Precursors for forming other metal oxide coatings described above via ALD and ALD reaction conditions are further described in U.S. Pub. No. 2015/0162602 to Dadheech et al., the relevant portions of which are hereby incorporated by reference.

ALD is typically conducted in an apparatus having a vacuum deposition chamber with a holder for the substrate, at least one vapor source (known as the precursor) and various controls by which the substrate may be individually subjected to the vapor source. Such controls may include heaters, coolers, flow routing and valves, for controlling the amount of exposure of the substrate to the vapor source. The regions of the substrate to be coated may be pre-treated, for example, by plasma treatment. The ALD process for deposition of surface coating onto the substrate involves reaction of the surface in a deposition chamber with a single vapor of precursor materials or reaction of the surface with multiple vapors introduced sequentially and having the precursors of the surface coating. Suitable precursors may include organic and inorganic metallic compounds. The vapor may be pulsed into the vacuum deposition chamber on a carrier gas and may be quickly purged, for example, by vacuum pumping or flushing with an inert gas. Such pulsing of the vapor and purging of the system may be performed to control the dose of the precursor vapor to which the substrate is exposed.

Generally, the ALD process is performed at elevated temperatures and reduced pressures. Temperature of the deposition chamber is desirably high enough that reaction between the substrate and the precursors in the vapor occurs, while also preventing condensation of the vapor onto the surface. As non-limiting examples, the reaction space in the deposition chamber may be heated to between about 50° C. and about 800° C., and the operating pressure may be between about $7.5 \times 10^{-2}$ Torr and about 4 Torr (about 1 Pa to about 5000 Pa).

As a result of ALD process and surface reactions, a single atomic layer of the surface coating material is bound to substrate surface, thereby providing a monoatomic coating. With sequential or alternating reactions, composite layers may be formed. Furthermore, additional atomic monolayers may be grown over the monoatomic layer, thereby forming a surface coating having greater thicknesses. The ALD process is illustrative of one technique for forming aluminum oxide ($Al_2O_3$) coatings on a substrate, but the process may also be used to form other coatings as well, by way of non-limiting example. For example, other oxide-based based coatings may be formed on the substrate via an ALD process. Moreover, various other coatings can be easily obtained by using different precursors and deposition processes.

In certain variations, the first vapor precursor may comprise aluminum. As a non-limiting example, the first vapor precursor may be selected from a group consisting of trimethyl aluminum (TMA (($CH_3)_3Al$)), triethyl aluminum (($C_2H_5)_3Al$), diethyl aluminum (($C_2H_5)_2AlCl$), tributyl aluminum (($C_4H_9)_3Al$), aluminum chloride ($AlCl_3$), aluminum ethoxide ($Al(OC_2H_5)_3$), aluminum isopropoxide ($Al(C_3H_7O)_3$), aluminum fluoride ($AlF_3$), aluminum nitride (($AlN$), where the precursor is TMA and ammonia). The second vapor precursor may comprise water vapor or a plasma. Suitable plasmas for ALD include argon (Ar), hydrogen ($H_2$), oxygen ($O_2$), nitrogen ($N_2$), and combinations thereof.

In one variation, the ALD process employs a first vapor precursor of trimethyl aluminum (TMA ($CH_3)_3Al$) and/or aluminum chloride ($AlCl_3$) and water vapor ($H_2O$) as a second vapor precursor, which forms aluminum oxide ($Al_2O_3$).

The photoactive layer 26 may be deposited on the nucleation material coating 24 by atomic layer deposition (ALD), chemical vapor deposition (CVD), including atmospheric pressure chemical vapor deposition (APCVD), low pressure chemical vapor deposition (LPCVD), plasma enhanced chemical vapor deposition (CVD), physical vapor deposition (PVD), such as magnetron sputtering, such as magnetron sputtering or radiofrequency (RF) sputtering, or other techniques known for depositing photocatalytic active materials, like titanium dioxide having an anatase crystal structure.

Where the titanium oxide ($TiO_2$) is applied via an ALD process, the precursor materials may be titanium n-butoxide (n-$C_4H_9O)_4Ti$), titanium t-butoxide (t-$C_4H_9O)_3Ti$), titanium chloride-aluminum chloride ($TiCl_3 \cdot \frac{1}{3}AlCl_3$), titanium (IV) chloride ($TiCl_4$), titanium (IV) isopropoxide ($C_3H_7O)_4Ti$), tetrakis(diethylamido)titanium(IV), and/or tetrakis(dimethylamido)titanium(IV), by way of example. Suitable non-limiting precursors for forming a titanium oxide coating via ALD comprise titanium tetrachloride ($TiCl_4$) and water ($H_2O$). For a titanium oxide coating ($TiO_2$), the precursor materials may be titanium tetrachloride ($TiCl_4$), tetrakis(diethylamido)titanium(IV), tetrakis(dimethylamido)titanium(IV), and/or titanium(IV) isopropoxide, by way of example. In one variation, suitable non-limiting precursors for forming a titanium oxide coating via ALD comprise titanium tetrachloride ($TiCl_4$) and water ($H_2O$). In another variation, magnetron sputtering may be conducted, for example, by using a titanium metal target, RF magnetron sputtering from ceramic $TiO_2$ targets, or may be direct deposition from a ceramic titanium dioxide target to form $TiO_2$ photoactive material. In such deposition techniques, Ti atoms, O atoms, and TiO species all impinge upon the surface and skate around to find their lowest energy configuration within kinetic constraints. Where the nucleation material template is in place to promote a $TiO_2$ crystal configuration corresponding to anatase, then the surface will be coated substantially with domains of anatase microcrystal.

Thus, in certain variations, a thin $Al_2O_3$ nucleation layer enhances the photonic efficacy and photocatalytic activity of $TiO_2$-containing active coatings. As noted above, the nucleation layer optimizes oriented nucleation growth required for the crystallinity and lattice matching with high adhesion and minimum stress. Including the $Al_2O_3$ based nucleation layer significantly improves the growth of anatase phase of $TiO_2$ enabling a high photocatalytic activity as compared to $TiO_2$ without the nucleation layer.

In certain variations, the presence of the nucleation material on the substrate enhances the photocatalytic activity of the photocatalytic active materials in the photoactive layer, as compared to the photocatalytic activity of a photocatalytic active material deposited directly on the substrate in the absence of the nucleation material coating. For example, the photocatalytic activity for a system including the nucleation material disposed on the substrate (having a substrate, a nucleation material, and a photoactive layer disposed thereon) in increased by greater than or equal to about 50% as compared to the system lacking the nucleation material layer, optionally the photocatalytic activity is greater than or equal to about 60% greater, optionally the photocatalytic activity is greater than or equal to about 70% greater, and in certain variations, optionally the photocatalytic activity is greater than or equal to about 75% greater. The photocatalytic activity can be measured by ISO standard 10678 "Determination of Photocatalytic Activity of Surfaces in an Aqueous Medium by Degradation of Methylene Blue" that measures temporal absorbance changes of methylene blue when in contact with the photocatalytic active material, such as $TiO_2$.

The substrate (e.g., substrate 22 in FIG. 1) may be formed of a variety of different substrates. In certain variations, the substrate comprises silicon dioxide ($SiO_2$), sodium borosilicate, soda-lime-silica glass, or other glasses. The substrate may be amorphous or crystalline. In certain aspects, the substrate may be formed of float glass. It should be noted that due to the presence of the thin nucleation material coating, a high quality photoactive material layer can be formed on a variety of substrates of varying quality, crystallinity, and surface roughness. In other aspects, the substrate may be a multilayered structure, such as an anti-reflection coating, which may have multiple layers with distinct refractive indices.

The substrate may be amorphous or crystalline. In certain aspects, the substrate may be formed of float glass. In other aspects, the substrate may be a multilayered structure, such as an anti-reflection coating, which may have multiple layers with distinct refractive indices.

Figure 2:
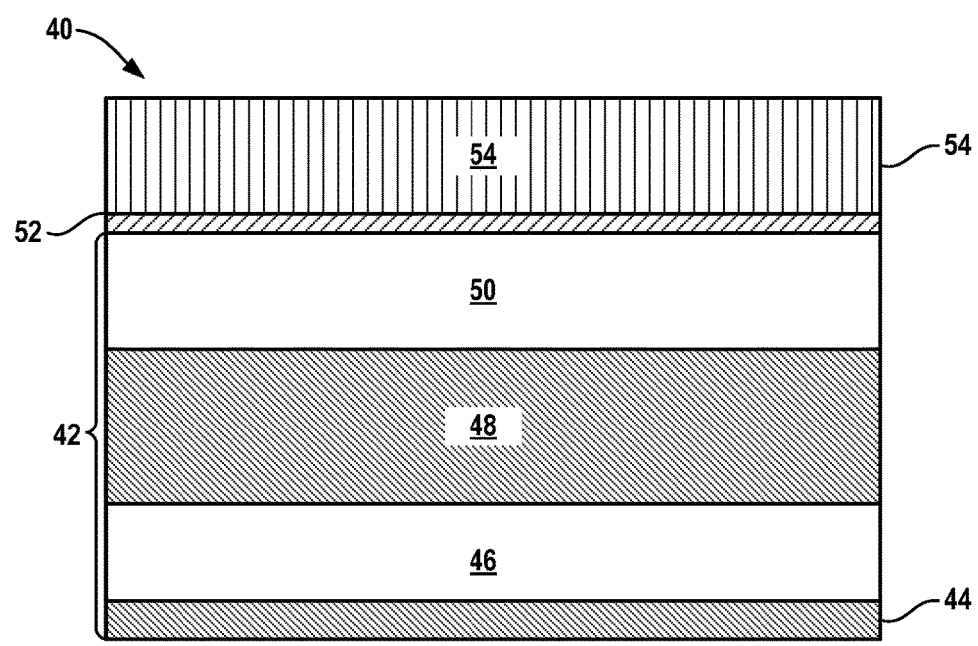
FIG. 2 shows a sectional side view of a photoactive system including a substrate that is an anti-reflection layered coating, a nucleation layer, and a photoactive layer prepared in accordance with certain other aspects of the present disclosure.

Such a self-cleaning system 40 is shown in FIG. 2, where a substrate 42 is in the form of an anti-reflection coating. By way of non-limiting example, an anti-reflection coating may have alternating layers of high refractive index material, like titanium dioxide ($TiO_2$), and low refractive index material, like silicon dioxide ($SiO_2$), with different thicknesses. By using alternating layers of a low-index material like silica and a higher-index material titania, it is possible to obtain reflectivity as low as 0.1% at a single wavelength. Such anti-reflection coatings can give very low reflectivity over a broad band.

In one embodiment, the antireflection coating may include a first layer 44 of $TiO_2$ (a high refractive index material) having a thickness of about 10 nm, a second layer 46 of $SiO_2$ (a low refractive index layer) having a thickness of about 33 nm, a third layer 48 of $TiO_2$ having a thickness of about 100 nm, and a fourth layer 50 of $SiO_2$ having a thickness of about 75 nm. A nucleation material coating 52 may be deposited or applied to the fourth layer 50 of the substrate 52 in the form of the anti-reflection coating. A photoactive layer 54 comprising a photocatalytic active material may be deposited over the nucleation material coating 52.

Figure 3:
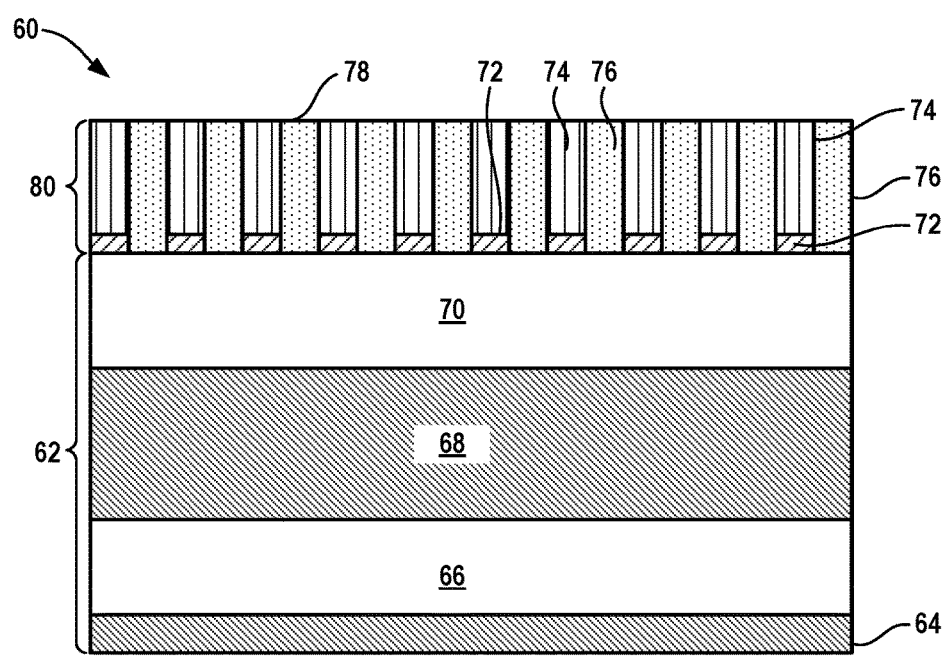
FIG. 3 shows a sectional side view of a photoactive system including a substrate and a self-cleaning surface that includes islands of a nucleation material and photocatalytic active material disposed within a low surface energy material prepared in accordance with yet other aspects of the present disclosure.

In other aspects, another self-cleaning system 60 is shown in FIG. 3, where a substrate 62 is also in the form of an anti-reflection coating. The antireflection coating may include a first layer 64 of $TiO_2$ (a high refractive index material) having a thickness of about 10 nm, a second layer 66 of $SiO_2$ (a low refractive index layer) having a thickness of about 33 nm, a third layer 68 of $TiO_2$ having a thickness of about 100 nm, and a fourth layer 70 of $SiO_2$ having a thickness of about 75 nm. In FIG. 3, a nucleation material coating 72 is disposed over discrete, non-contiguous, select regions of the fourth layer 70. A photoactive coating 74 comprising a photocatalytic active material is disposed over the discrete, non-contiguous, select regions where the nucleation material coating 72 is disposed over the fourth layer 70.

A low surface energy material 76 is also disposed within select regions of the fourth layer 70 and is disposed between the discrete, non-contiguous, select regions where the nucleation material coating 72 and photoactive coating 74 are applied on the fourth layer 70. In this manner, the nucleation material coating 72 and photoactive coating 74 define distinct islands within the low surface energy material 76. The low surface energy material 76 may define a contact angle with water of greater than 110°, optionally greater than or equal to about 115°, optionally greater than or equal to about 120°, optionally greater than or equal to about 125°, optionally greater than or equal to about 130°, optionally greater than or equal to about 135°, and in certain variations, optionally greater than or equal to about 150°. As such, water, oils, and contaminants may effectively bead on and may be mobile, translating across an exposed surface 78 defined by the low surface energy material 76 having the islands of photoactive coating 74 disposed therein.

The low surface energy material 76 may be a fluoropolymer. By way of non-limiting example, the fluoropolymer may be a perfluorocarbon siloxane. In one embodiment, the perfluorocarbon siloxane polymer is a polytetrafluoroethylene (PTFE) siloxane polymer. In certain aspects, the low surface energy material 76 may be applied as a thin layer, for example, as a monolayer having a thickness of one molecule.

A method of forming the self-cleaning system 60 may include depositing a perfluorocarbon siloxane polymer onto the substrate 62 in a continuous layer. It should be noted that the substrate 62 need not be an anti-reflection multilayered coating as shown in FIG. 3. In one example method, the nucleation material coating 72 and photoactive coating 74 can be applied continuous films or layers. Then, photolithographic methods can be used to pattern the layers of nucleation material coating 72 and photoactive coating 74 to produce islands of photoactive coating 74 separated by bare substrate 62. Before removal of the photoresist from atop the photoactive coating 74, the low surface energy material 76, such as perfluorocarbon siloxane polymer, may be subsequently deposited. The may be deposited or coated onto the substrate 62 in any suitable manner. By way of non-limiting examples, depositing of the low surface energy material may occur by chemical vapor depositing (CVD), atomic layer deposition (ALD), dipping, wiping, spraying, meniscus coating, wet coating, combinations and equivalents thereof. Depositing may include forming a self-aligned monolayer that is physically adsorbed, i.e., physisorbed, and cross-linked with neighboring molecules through a siloxane moiety. After application of the low surface energy material 76, the photoresist can be removed by dissolution to form a self-cleaning layer or film 80. Generally, the photocatalytic active material in the photoactive coating 74 may be present in the self-cleaning film 80 in an amount of from about 2 parts by volume to about 35 parts by volume based on 100 parts by volume.

In certain aspects, the self-cleaning photocatalytic systems provided in accordance with certain aspects of the present disclosure enable disappearance or removal of visible fingerprints and other visible residue from an exposed surface, which is a function of UV flux. The self-cleaning photocatalytic systems provided in accordance with certain aspects of the present disclosure enable disappearance or removal of visible fingerprints and other visible residue from an exposed surface (e.g., in an interior of a vehicle) in less than or equal to about 4 hours, optionally less than or equal to about 3 hours, optionally less than or equal to about 2 hours, optionally less than or equal to about 1.5 hours, optionally less than or equal to about 1 hour, optionally less than or equal to about 45 minutes, optionally less than or equal to about 45 minutes, and in certain variations, optionally less than or equal to about 20 minutes.

Various embodiments of the present technology can be further understood by the specific examples contained herein. Specific Examples are provided for illustrative purposes of how to make and use the compositions, devices, and methods according to the present teachings and, unless explicitly stated otherwise, are not intended to be a representation that given embodiments of this invention have, or have not, been made or tested.

EXAMPLE 1

Methylene Blue Degradation via the Photocatalytic Activity of $TiO_2$ Films by use of ISO Standard 10678—a Method for Quantifying Photocatalytic Activity of Materials Using the Elimination of Solution Phase Methylene Blue. As noted above, ISO 10678 specifies measuring temporal absorbance changes of a methylene blue in contact with the material ($TiO_2$, in this example).

Experimental Conditions are as follows. A Methylene Blue (MB) solution is provided in a column having a height of 50 mm. A concentration/initial absorbance is 0.74. A light source used is an ultraviolet (UV) black light where irradiance is 4 mW/sq.cm.

A first Control sample labeled 110 has a float glass substrate on which a titanium dioxide ($TiO_2$) layer is directly deposited via a MS, ALD/APCVD process. The Control 110 is maintained under the sample conditions while disposed in the MB solution, but is not exposed to UV (dark sample). The ALD precursors for $TiO_2$ are $TiCl_4$ and/or titanium isopropoxide.

A second comparative sample labeled 112 includes a $TiO_2$ film disposed on a float glass substrate. The $TiO_2$ layer is deposited via an atomic layer deposition via ALD with the precursor above directly onto the substrate surface. The $TiO_2$ photoactive layer has an average thickness of about 10 nm. It is believed that directly depositing the $TiO_2$ onto the glass substrate via ALD process creates a $TiO_2$ layer comprising a combination of brookite, rutile, and minor amounts of anatase.

A third sample labeled 114 includes a nucleation layer comprising $Al_2O_3$ disposed on a float glass substrate in accordance with certain aspects of the present disclosure. The $Al_2O_3$ is deposited via an atomic layer deposition with precursor described above and has a thickness of about 5 nm. Under such conditions, it is believed that primarily a $\theta$-$Al_2O_3$ phase is formed. Then, a $TiO_2$ film is deposited over the $Al_2O_3$ via an ALD process directly onto the substrate surface. The $TiO_2$ photoactive layer has an average thickness of about 10 nm. The amount of anatase formed in the $TiO_2$ film over the $Al_2O_3$ template is significantly increased as compared to the second comparative sample 112.

Figure 4:
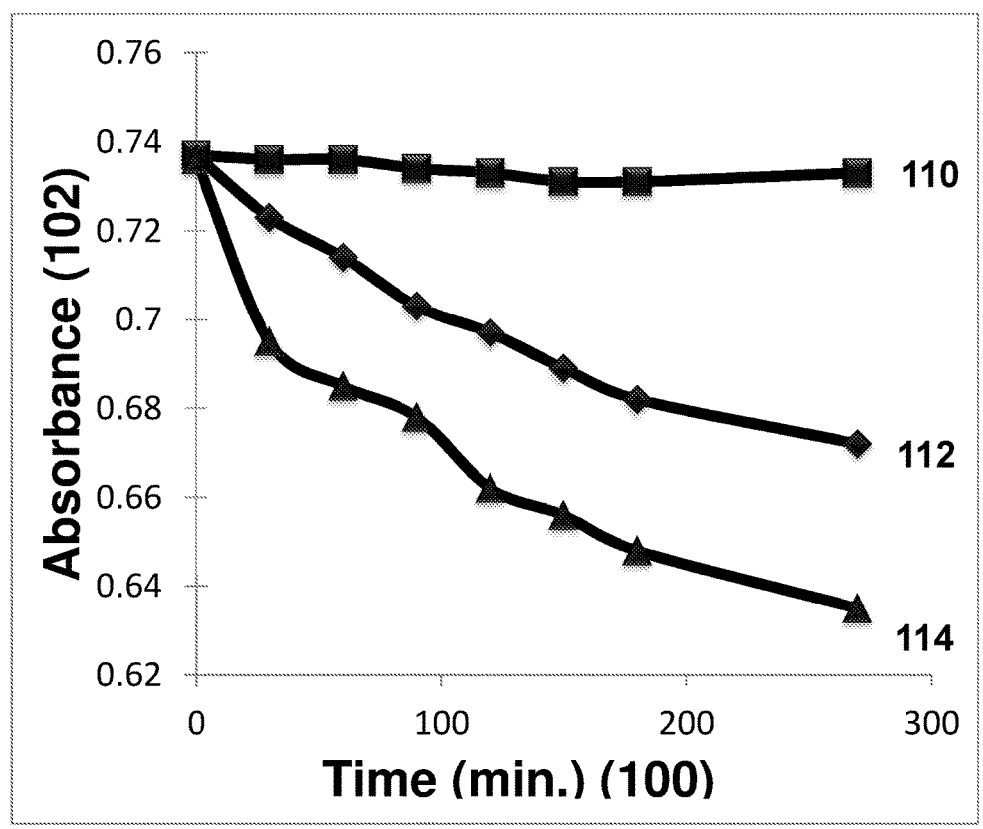
FIG. 4 shows a comparative chart of photocatalytic activity for Methylene Blue (absorbance versus time) of a photoactive system prepared in accordance with certain aspects of the present disclosure compared to a control and a comparative sample lacking a nucleation layer.

FIG. 4 shows time 100 versus absorbance 102 measuring Methylene Blue (MB) degradation via photocatalytic activity. 14% of the MB is decomposed via photocatalysis by the $TiO_2$ on an alumina nucleation layer after 4 hours as shown for Sample 114. By way of comparison, 8% of the MB is decomposed via photocatalysis by $TiO_2$ without an alumina nucleation layer after 4 hours for Sample 112. Therefore, use of an $Al_2O_3$ nucleation layer in Sample 114 increases the photocatalytic activity of ALD grown $TiO_2$ films by about 75%.

Rate constants for the photocatalytic degradation of MB for the third sample labeled 114 and second comparative sample 112 are believed to be as follows. A pseudo first order rate constant for Sample 114 is $4.97 \times 10^{-4}$ mol/liter/s, whereas the rate constant for Sample 112 is $3.44 \times 10^{-4}$ mol/liter/s. Thus, under experimental conditions (light flux, MB pH, and temperature) the $Al_2O_3$ nucleation layer increases the rate constant by a factor of about 1.45.

As such, the present disclosure provides excellent photocatalytic activity for $TiO_2$ films due to the presence of a primer nucleation layer of $Al_2O_3$, which improves the c-axis crystal growth providing the desired crystallinity, texture and conformability of $TiO_2$ coatings. Such a process may be readily scaled and used in a continuous manufacturing process.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A photocatalytic system comprising:
   a nucleation material coated on a substrate, wherein the nucleation material comprises a metal oxide compound, wherein the metal is selected from the group consisting of: aluminum, zirconium, niobium, cerium, vanadium, lanthanum, titanium, silicon, iron, cobalt, nickel, molybdenum, tungsten, and combinations thereof, and wherein the nucleation material has an average thickness of less than or equal to about 10 nm; and
   a photocatalytic active material comprising an anatase phase of titanium dioxide ($TiO_2$) deposited over the nucleation material, wherein a photocatalytic activity is greater than or equal to about 50% above a comparative photocatalytic activity where the photocatalytic active material is disposed directly on the substrate.

2. The photocatalytic system of claim 1, wherein the nucleation material is selected from the group consisting of: aluminum oxide ($Al_2O_3$), $SrTiO_3$ (STO), $LaAlO_3$ (LAO), Y stabilized $ZrO_2$ (YSZ), and combinations thereof.

3. The photocatalytic system of claim 1, wherein the nucleation material comprises aluminum oxide ($Al_2O_3$).

4. The photocatalytic system of claim 3, wherein the aluminum oxide ($Al_2O_3$) comprises a $\theta$-$Al_2O_3$ phase having a monoclinic space group with lattice parameters of a=1.185 nm, b=0.295 nm and c=0.562 nm.

5. The photocatalytic system of claim 1, wherein a lattice mismatch is less than or equal to about 12% between the nucleation material and the photocatalytic active material.

6. The photocatalytic system of claim 1, wherein the active material comprises greater than or equal to about 50% by volume of anatase phase.

7. The photocatalytic system of claim 1, wherein the photocatalytic activity is greater than or equal to about 75% above the comparative photocatalytic activity where the active material is disposed directly on the substrate.

8. A self-cleaning photocatalytic system comprising:
   a substrate;
   a nucleation coating comprising aluminum oxide ($Al_2O_3$) disposed on the substrate having a thickness of less than or equal to about 10 nm; and an exposed surface comprising a photocatalytic active material that comprises an anatase phase of titanium dioxide ($TiO_2$) deposited over the nucleation coating, wherein the photocatalytic active material facilitates a decomposition reaction of any oil or organic residue on the exposed surface when in the presence of water and ultraviolet radiation.

9. The self-cleaning photocatalytic system of claim 8, wherein a photocatalytic activity of the self-cleaning photocatalytic system is greater than or equal to about 50% above a comparative photocatalytic activity where the photocatalytic active material is disposed directly on the substrate.

10. The self-cleaning photocatalytic system of claim 8, wherein the nucleation coating has an average thickness of greater than or equal to about 3 nm to less than or equal to about 5 nm.

11. The self-cleaning photocatalytic system of claim 8, wherein the photocatalytic active material comprises greater than or equal to about 50% by volume of the anatase phase of titanium dioxide ($TiO_2$).

12. The self-cleaning photocatalytic system of claim 8, wherein the substrate comprises glass or an anti-reflection coating.

13. The self-cleaning photocatalytic system of claim 8, wherein the exposed surface defines a plurality of islands of the photocatalytic active material distributed within a low surface energy polymeric material, wherein the nucleation coating is disposed beneath the photocatalytic active material, but is absent in regions where the low surface energy polymeric material is present.

14. The self-cleaning photocatalytic system of claim 8, wherein a lattice mismatch is less than or equal to about 2% between the nucleation coating and the photocatalytic active material.

15. The self-cleaning photocatalytic system of claim 8, wherein the aluminum oxide ($Al_2O_3$) comprises a $\theta$-$Al_2O_3$ phase having a crystal structure having a monoclinic space group with lattice parameters of a=1.185 nm, b=0.295 nm and c=0.562 nm that enhances lattice matching and formation of the anatase phase of titanium dioxide ($TiO_2$).

16. A method of enhancing photocatalytic activity in a photocatalytic system comprising:
   depositing a nucleation material coated on a substrate, wherein the nucleation material comprises a metal oxide compound, wherein the metal is selected from the group consisting of aluminum, zirconium, niobium, cerium, vanadium, lanthanum, titanium, silicon, iron, cobalt, nickel, molybdenum, tungsten, and combinations thereof, and wherein the nucleation material has an average thickness of less than or equal to about 10 nm; and
   depositing a photocatalytic active material comprising an anatase phase of titanium dioxide ($TiO_2$) over the nucleation material, wherein the nucleation material provides lattice matching to enhance formation of the anatase phase of titanium dioxide ($TiO_2$), so that a photocatalytic activity is greater than or equal to about 50% above a comparative photocatalytic activity where the photocatalytic active material is disposed directly on the substrate.

17. The method of claim 16, wherein the depositing of the nucleation material is a process selected from the group consisting of: atomic layer deposition (ALD), chemical vapor deposition (CVD), plasma enhanced chemical vapor deposition (CVD), physical vapor deposition (PVD), and combinations thereof.

18. The method of claim 16, wherein the depositing of the photocatalytic active material is a process selected from the group consisting of: atomic layer deposition (ALD), chemical vapor deposition (CVD), atmospheric pressure chemical vapor deposition (APCVD), low pressure chemical vapor deposition (LPCVD), plasma enhanced chemical vapor deposition (CVD), physical vapor deposition (PVD), magnetron sputtering, wet chemistry, sol-gel processes, and combinations thereof.

19. The method of claim 16, wherein the depositing of the nucleation material is done by an atomic layer deposition process.

* * * * *